United States Patent
Cornacchia, III

(10) Patent No.: US 7,877,683 B2
(45) Date of Patent: Jan. 25, 2011

(54) SELF-ORGANIZING REPORT

(76) Inventor: Louis G. Cornacchia, III, 110 Ocean Boulevard, Point Lookout, NY (US) 11569

( * ) Notice: Subject to any disclaimer, the term of this patent is extended or adjusted under 35 U.S.C. 154(b) by 1210 days.

(21) Appl. No.: 11/498,955

(22) Filed: Aug. 3, 2006

(65) Prior Publication Data

US 2007/0038948 A1 Feb. 15, 2007

Related U.S. Application Data

(63) Continuation-in-part of application No. 11/083,865, filed on Mar. 18, 2005.

(51) Int. Cl.
G06F 17/21 (2006.01)
(52) U.S. Cl. .................................... 715/255
(58) Field of Classification Search ................ 715/255, 715/201, 205, 210, 229
See application file for complete search history.

(56) References Cited

U.S. PATENT DOCUMENTS

| | | | |
|---|---|---|---|
| 6,031,625 A * | 2/2000 | Sherman et al. ........... | 358/1.18 |
| 6,177,940 B1 * | 1/2001 | Bond et al. ................. | 434/262 |
| 6,631,402 B1 * | 10/2003 | Devine et al. .............. | 709/217 |
| 6,632,251 B1 * | 10/2003 | Rutten et al. ............... | 715/205 |
| 6,684,188 B1 * | 1/2004 | Mitchell et al. ............ | 705/3 |
| 7,529,685 B2 * | 5/2009 | Davies et al. ............... | 705/3 |
| 7,549,118 B2 * | 6/2009 | Shur et al. .................. | 715/234 |
| 7,584,103 B2 * | 9/2009 | Fritsch et al. .............. | 704/257 |
| 7,617,450 B2 * | 11/2009 | Jones et al. ................. | 715/255 |
| 7,716,072 B1 * | 5/2010 | Green et al. ................ | 705/3 |
| 7,734,480 B2 * | 6/2010 | Stangel ...................... | 705/3 |
| 2002/0099552 A1 * | 7/2002 | Rubin et al. ................ | 704/270 |
| 2002/0111932 A1 * | 8/2002 | Roberge et al. ............ | 707/1 |
| 2005/0005233 A1 * | 1/2005 | Kays et al. ................. | 715/500.1 |
| 2005/0209892 A1 * | 9/2005 | Miller ......................... | 705/4 |
| 2006/0048096 A1 * | 3/2006 | Jiang et al. ................. | 717/115 |
| 2007/0150241 A1 * | 6/2007 | Critz et al. .................. | 703/2 |
| 2007/0196909 A1 * | 8/2007 | Showalter et al. ......... | 435/283.1 |

* cited by examiner

*Primary Examiner*—Doug Hutton
*Assistant Examiner*—Nathan Hillery

(57) ABSTRACT

A computer-based method for generating a report. The computer-based method includes: initializing a plurality of report parameters; determining a report editing mode based a selected report editing mode; generating a filtered list of report components based on the plurality of report parameters and the report editing mode; determining a report component based on selection from the filtered list of report components; and inserting the report component into the report at a predetermined first position derived from a first priority of the report component.

13 Claims, 14 Drawing Sheets

SELF-ORGANIZING REPORT

CROSS-REFERENCE TO RELATED PATENT APPLICATION

This is a Continuation-In-Part Application of U.S. application Ser. No. 11/083,865, filed Mar. 18, 2005 and entitled "SYSTEM AND METHOD FOR REMOTELY INPUTTING AND RETRIEVING RECORDS AND GENERATING REPORTS," the content of which is herein incorporated by reference in its entirety.

BACKGROUND OF THE INVENTION

1. Technical Field

The present disclosure relates to methods and systems for generating a report.

2. Discussion of the Related Art

It has been the practice of professionals, such as doctors, lawyers, and engineers to personally record pertinent information on a subject patient, client or matter so that professional services performed and data pertinent to the subject are documented. In many instances, the professional memorializes the pertinent data or basis for a decision contemporaneously as services are performed, such as by handwritten notes or dictation into a voice recorder, and the information is subsequently gathered for office personnel to enter into a report. Many reports are standardized as forms and the gathered information is filled into the form for efficient reporting. Record documentation is commonly prepared manually using predefined paper templates. Using traditional records management practices, data is not readily available to users. Data on paper forms cannot be easily combined with other reports containing data for analysis and reporting.

Some electronic medical records systems use hard-coded medical report templates or require the user to build the reports and organize the sections manually. Those prior art systems force the user to document according to a set of defined templates. This means, for example, that an actual medical report may contain several blank sections because some predefined sections were not needed for a particular medical visit. In addition, the user may be forced to include manual addenda with relevant clinical information that is not accounted for in the system's set of template forms. Electronic medical records systems that do allow for user customization of medical report templates either do not allow such customization while a report is being edited, or force the user to define the physical position of newly inserted sections.

U.S. Pat. No. 5,267,155 describes a document generation system, which automates the documentation process in the medical field. The system provides a computer-based documentation system incorporating a retrievable database with a menu driven graphical window environment. The documentation system utilizes previously defined document templates or "boiler-plates" to manage patient reports and includes a user interface for selecting phrases to be inserted into the template.

U.S. Pat. No. 6,026,363 discloses a medical history documentation system and method for recording information relating to at least one of a designated patient's current medical condition, a physical examination, a diagnosis and a treatment plan. The system includes a transcriber for providing a plurality of report section templates. Each of the report section templates comprise a plurality of optional text variable segments. The patient report comprises a combination of selected optional text variable segments.

Despite the advances in the art, there is a need for a system and method of generating reports more easily.

SUMMARY OF THE INVENTION

According to an exemplary embodiment of the present invention, a computer-based method is provided for generating a report. The method includes: initializing a plurality of report parameters; determining a report editing mode based on a selected report editing mode; generating a filtered list of report components based on the plurality of report parameters and the report editing mode; determining a report component based on selection from the filtered list of report components; and inserting the report component into the report at a pre-determined first position derived from a first priority of the report component.

According to another exemplary embodiment of the present invention, there is provided a computer-based method for building a template for use in generating a report. The computer-based method includes: determining a report component based on user input for insertion into the template, wherein the report component is inserted into the template at a position relative to a priority of the report component and priorities of all siblings of the report component; determining a template name from user input; and storing the template using the template name.

According to another exemplary embodiment of the present invention, there is provided a computer readable medium including computer code for generating a report, the computer readable medium comprising: computer code for initializing a plurality of report parameters; computer code for determining a report editing mode based on a selected report editing mode; computer code for generating a filtered list of report components based on the plurality of report parameters and the report editing mode; computer code for determining a report component based on selection from the filtered list of report components; and computer code for inserting the report component into the report at a pre-determined first position derived from a first priority of the report component.

According to an exemplary embodiment of the present invention, there is provided a computer-based method of generating a report component to be used in an electronic report. The computer-based method includes the steps of selecting a name for the report component, selecting a hierarchical value for the report component which represents a hierarchical level, and selecting a priority for the report component which is used to order the report component relative to a second report component with the same hierarchical value.

The present invention will become more apparent to those of ordinary skill in the art when descriptions of exemplary embodiments thereof are read with reference to the accompanying drawings.

DESCRIPTION OF EXEMPLARY EMBODIMENTS

Figure 1:
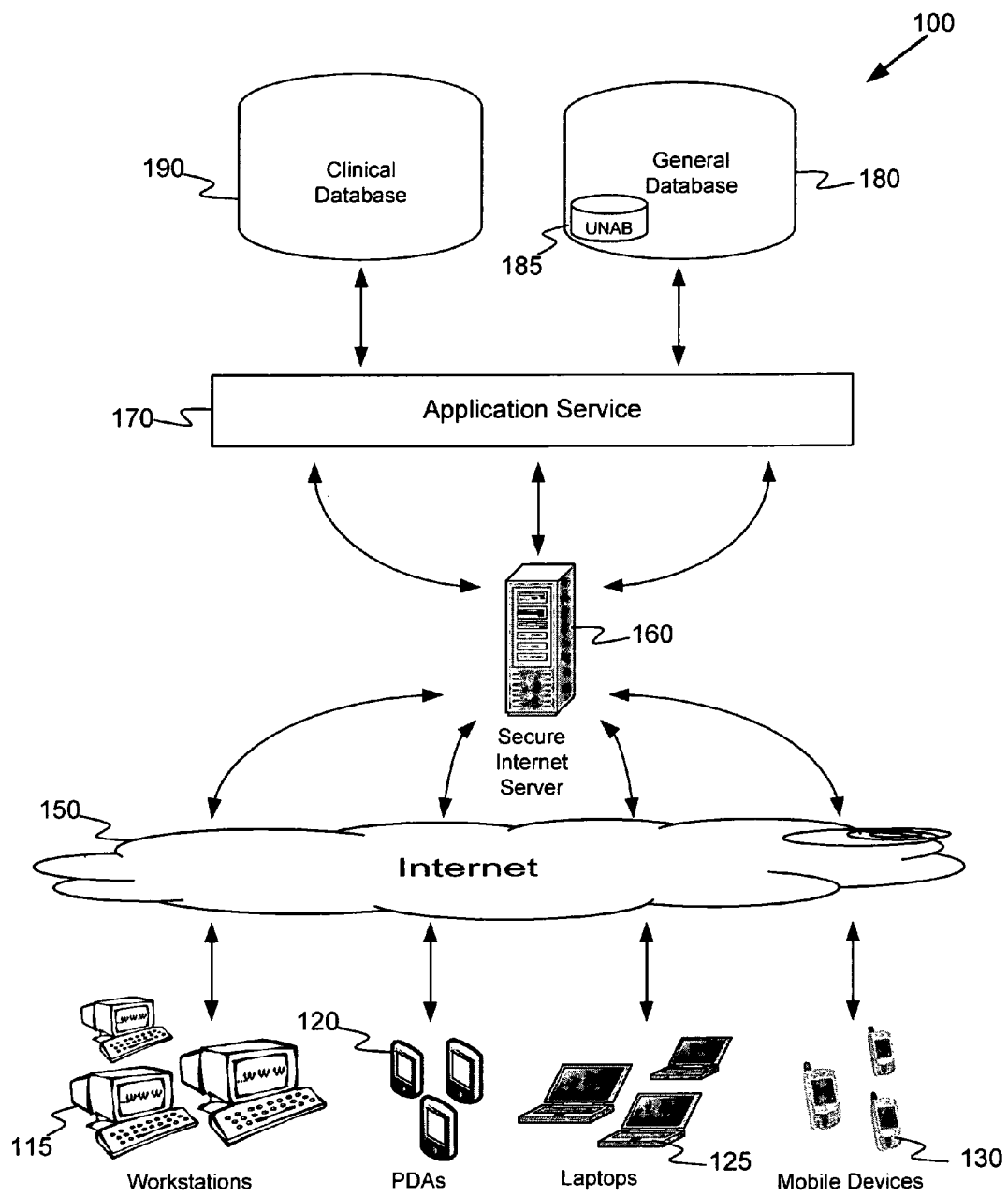
FIG. 1 illustrates a computer network suitable for use in accordance with an exemplary embodiment of the present invention.

Hereinafter, exemplary embodiments of the present invention will be described in detail with reference to the accompanying drawings. Like reference numerals refer to similar of identical elements throughout the description of the figures.

FIG. 1 illustrates a computer network suitable for use in accordance with an exemplary embodiment of the present invention. It should be understood that the elements shown in FIG. 1 may be implemented in various forms of hardware, software or combinations thereof.

Referring to FIG. 1, a computer network 100 includes clinical database 190, general database 180, application service 170, secure Internet server 160, and at least one Internet access device, such as for example, workstation 115, PDA 120, laptop (or notebook) computer 125, or other Microsoft Windows-enabled mobile devices 130. The computer network 100 also includes a software subsystem called the "universal address book", which maintains information on all entities in the system. In an exemplary embodiment of the present invention, universal address book (UNAB) data 185 is contained in the general database 180. The information such as person identifying and demographic information stored in the general database 180 may be separated from the data that is stored in the clinical database 190. The general database 180 is designed to be run either integrated with the other database tables or hosted as a separate database system in a geographically different site from the clinical database 190. When hosted separately, a hacker who succeeds at hacking into one site will not obtain the other's information. For example, if a hacker were to hack into the clinical database 190 the hacker would not have the person identifying information. To increase security and privacy, the demographic data and/or clinical data may be encrypted. The connection between the UNAB and the clinical database 190 may also be encrypted.

The secure Internet server 160 includes modules to facilitate access to/from application service 170 to the various Internet access devices 115, 120, 125 and 130 connected to the network over the Internet 150. The workstations 115, for example, may be a fixed or portable personal computer equipped with a computer monitor or screen, a keyboard, a microphone and/or a camera, software modules for browsing hypertext or hypermedia pages, a set of computer speakers and a computer mouse.

Generally, data or information can be input into the secure Internet server 160 from the various Internet access devices 115, 120, 125 and 130 over the Internet 150 without software specially made for the secure Internet server 160. Specific software that may be needed from time to time can be downloaded from the secure Internet server 160 and installed at the various Internet access devices 115, 120, 125 and 130. For example, security software for user identification or authentication can be loaded at the user's station and used to ensure the user is a registered subscriber. Commercially available software such as VoiceID or Pronexus VBVoice can be used for the speaker identification process.

Figure 2:
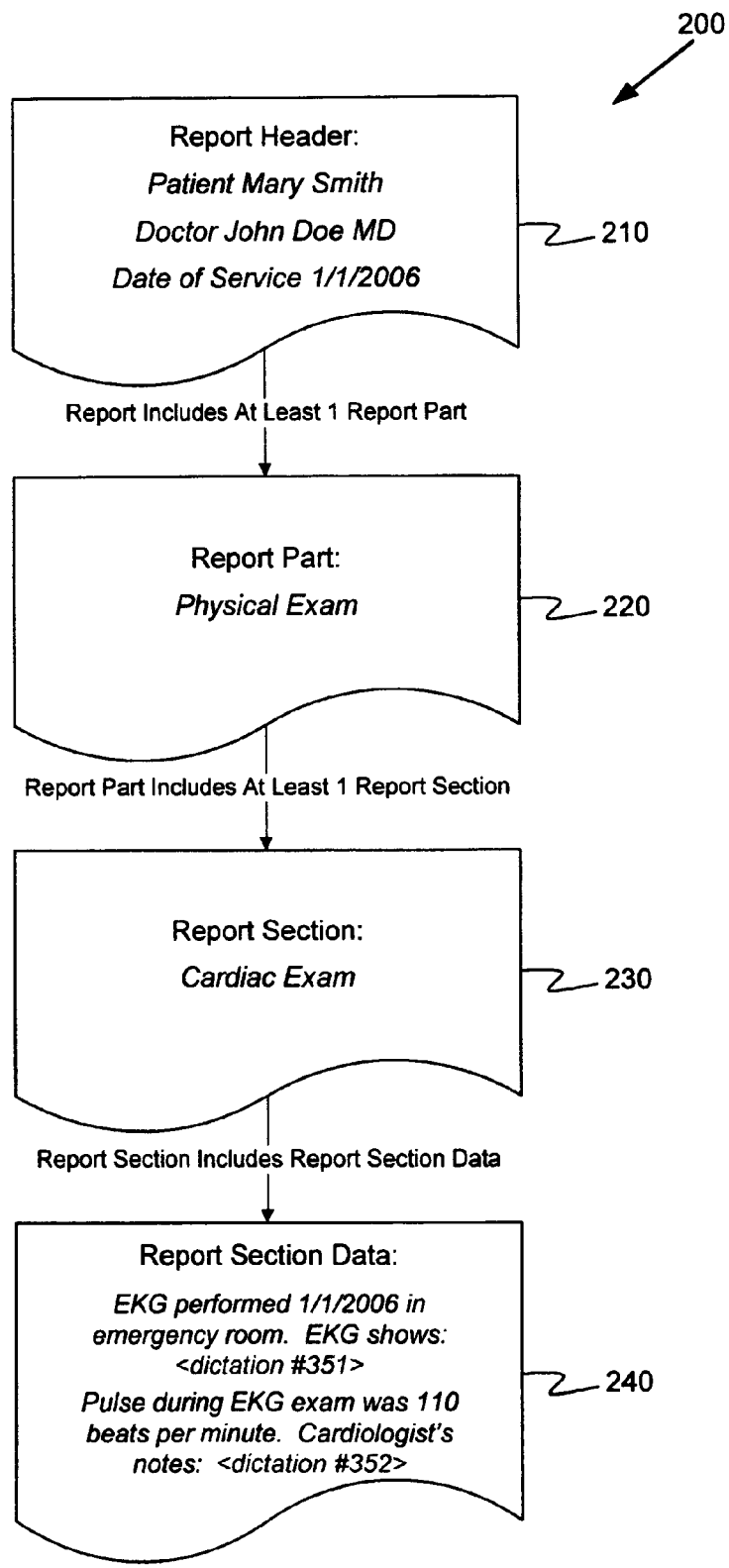
FIG. 2 illustrates a report structure showing a medical report header, part, section and section data, according to an exemplary embodiment of the present invention.

FIG. 2 illustrates a report structure including a medical report header, part, section and section data, according to an exemplary embodiment of the present invention. It will be appreciated that various types of reports are suitable for use in accordance with embodiments of the present invention, including but not limited to medical reports, engineering reports, research reports, business reports, insurance reports, financial reports, government reports, accident reports, client reports, tax reports, accounting reports, inventory reports, documentation reports, etc. Referring to FIG. 2, the report structure 200 illustrates an exemplary medical report that includes report header 210, report part 220, report section 230 and report section data 240.

A report, in accordance with an exemplary embodiment of the present invention, includes a report header 210, at least one report part 220, and at least one report section 230. The report header 210 may contain metadata relating to the entire report, such as for example, person, patient, client, author, entity such as a government entity, physician, engineer, attorney, date, file identifier such as project name, attorney docket number or security classification level, location and so forth.

In the case of a medical report, for example, there may be a report part 220 entitled physical exam. The physical exam part may contain sections for the chest exam, cardiac exam, abdominal exam, etc. A report section 230 may contain report section data 240. For example, in a medical report, each report section 230 contains clinical data that documents the information relevant to that section. For example, the data for the cardiac exam section may contain information about an EKG, resting pulse, etc. The section data can include data that was entered by various means, such as text entry and dictation(s). Examples of methods of dictating into a report section suitable for use in the present invention are disclosed in co-owned, co-pending U.S. patent application Ser. No. 11/498, 956, entitled "DICTATE SECTION DATA", the disclosure of which is herein incorporated by reference in its entirety.

Figure 3:
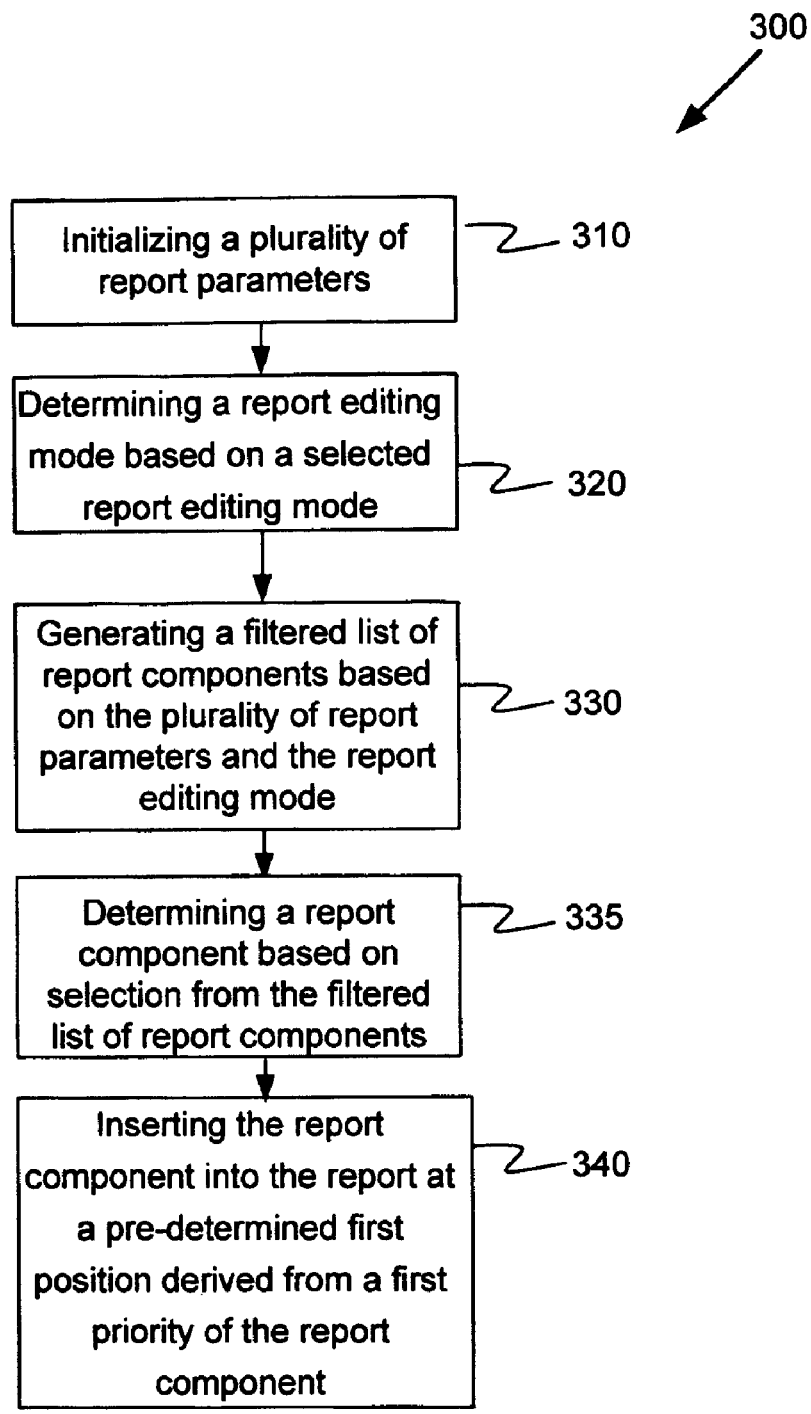
FIG. 3 is a flowchart illustrating a computer-based method of generating a report, according to an exemplary embodiment of the present invention.

FIG. 3 is a flowchart illustrating a computer-based method of generating a report, according to an exemplary embodiment of the present invention.

Referring to FIG. 3, in a step 310, a plurality of report parameters are initialized. For example, initializing report parameters may comprise providing user identifying information, providing date of service, providing location of service, providing organization information, providing client identifying information, providing report subject matter information, and/or providing account information.

In a step 320, a report editing mode is determined based on a selected report editing mode. For example, determining a report editing mode may comprise determining whether a new report choice or an existing report choice has been selected from user input. If a new report choice has been selected, a report type may be determined by selecting the report type from a list of pre-defined report types. The list of pre-defined report types may be filtered based on data contained within the report parameters that were initialized. On the other hand, if an existing report choice has been selected, selecting an existing report from a list of pre-defined existing reports and retrieving the report type from the selected existing report may determine the report type. Exemplary report types for a medical report may include but are not limited to message, consult, operating report, narrative report, administrative, admission, E&M, correspondence, surgical reports, discharge summary reports, etc. It is to be understood that the report types are not limited to those generally used in the medical field, as they often vary considerably based on the field the report is used in.

In a step 330, a filtered list of report components is generated based on the plurality of report parameters and the report editing mode. In a step 335, a report component is determined based on selection from the filtered list of report components. The report component may be determined by selecting a report component from a list of available report components. The list of report components may be filtered based on the data contained within the report parameters that were initialized and the determined report type.

In a step 340, the report component is inserted into the report at a pre-determined first position derived from a first priority of the report component, thereby obviating the need by the user to select where in the report the report component should be positioned. The pre-determined first position may be determined based on the first priority relative to priorities of other sibling report components already present within the report. A sibling report component is a report component in the report at a level equal to the hierarchical level of the report component to be inserted into the report.

The first priority may be a single numerical value. For example, if the first report priority were 1 and a priority of a sibling report component was 2, the report component would be inserted into the report before the sibling report component. The first priority may also comprise a set of relative rules. For example, if the first priority were 'always after sibling report component a' and 'always before sibling report component b', the report component would be inserted between sibling report components a and b.

Additional report components associated with the inserted report component may be automatically inserted into the report when the report component is inserted. For example, a report subpart called neurological may typically have report subsections for speech and gait, and inserting speech could automatically insert gait.

A report header containing information about the report and derived from the report parameters may be automatically inserted into a new report. An exemplary report header for a medical report may include various fields but are not limited to patient id, patient name, date of birth, provider id, provider name, organizational information, location of service, etc.

A report component may be the child of an ancestor (parent) report component. If a report component has an ancestor, it may be inserted into a nearest ancestor of the report component at a pre-determined first position based on an ancestor priority relative to priorities of other sibling report components already present within the nearest ancestor. A report component at the highest hierarchical level in the report has no ancestors. Ancestors of a report component from highest level to lowest hierarchical level, not already present in a report, may be automatically inserted into the report when the report component is inserted into the report.

A report component with a priority equal to a sibling report component may be inserted into a nearest ancestor of the report component at a pre-determined first position in the report based on the relative alphabetic order of the report component and the sibling report component.

Figure 4:
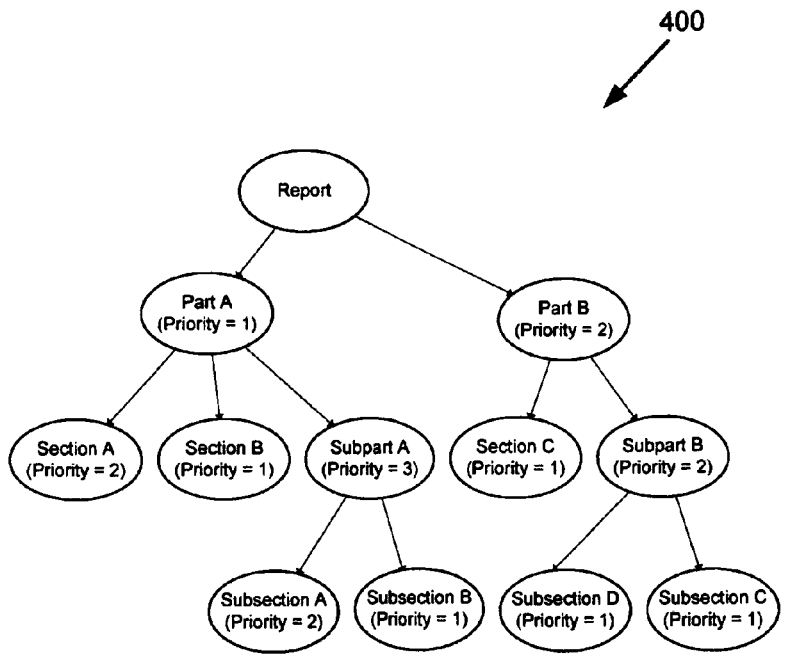
FIG. 4 is a tree diagram illustrating a hierarchy of report components according to an exemplary embodiment of the invention.

FIG. 4 is a tree diagram illustrating a hierarchy of report components according to an exemplary embodiment of the invention. Referring to FIG. 4, the tree 400 illustrates a report with four generational levels. A report may be comprised of report parts, report sections, report subparts, and report subsections. At the root of the tree is the report. Report parts reside at the second level of the tree, as children of the report. The third level consists of report sections and report subparts, which are children of a report part. The report sections and report subparts may be siblings within a report part. The report sections differ from the subparts in that report sections cannot have any children. The final level consists of report subsections, which are children of a report subpart. The report subsections do not have children like the report sections.

Figure 5:
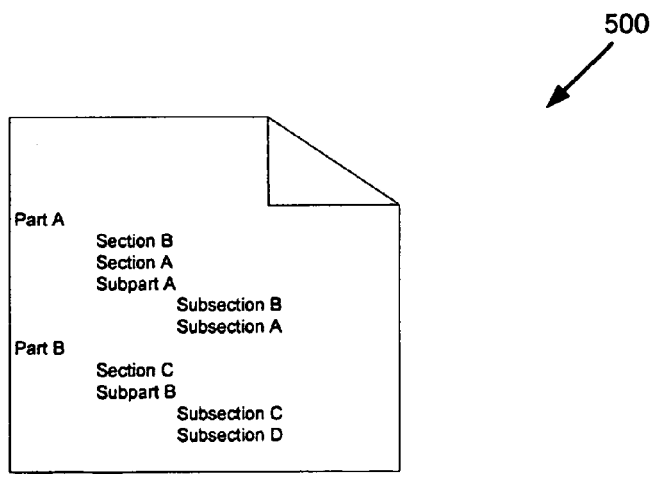
FIG. 5 illustrates a report generated from the tree diagram of FIG. 4, according to an exemplary embodiment of the present invention.

Each report component may have an associated priority. The associated priority is set based on established medical reporting procedures. Typically a Chief Complaint section will come before a Medical History section because standard logical medical procedure dictates that a physician inquire about a patient's chief complaint before delving into their medical history. As an example, the Chief Complaint section would be set to a priority of 1, while a Medical History section would be set to a priority of 2. The associated priority may be relative to a sibling report component priority. In the prior example, the Chief Complaint section and the Medical History section are siblings because they have the same parent report part History. Had the Medical History already been inserted into a medical report, a subsequent insertion of the Chief Complaint section would have inserted the Chief Complaint section above the Medical History section since a priority of 1 is lower than a priority of 2. By varying each report component priority, the appearance of a report may vary accordingly. FIG. 5 illustrates a report generated from the tree diagram of FIG. 4 according to an exemplary embodiment of the present invention.

Referring to FIG. 5, a first report component with a priority lower than a second report component at the same generation (also known as a sibling) appears below the second report component in the report 500. The report component ordering in FIG. 5 is merely an example for reference, as the report components can be ordered in a number of ways. Referring to FIG. 4, the report priority of part A is 1, while the report priority of part B is 2. Since 1 is less than 2, report part A appears before report part B in the report. When a report component has a priority identical to a sibling report component, there is a tie. In an exemplary embodiment of the invention, when a tie occurs, the report components are ordered alphabetically. Referring to FIG. 5, subsection C and D have the same priority, however subsection C appears before subsection D in the report because C appears before D in the alphabet. In FIG. 5, although a report component appears indented relative to its ancestor to denote the relationship, the relationship can be displayed by employing a number of representative schemes including color, bolding, underlining, italics, font, etc.

Figure 6:
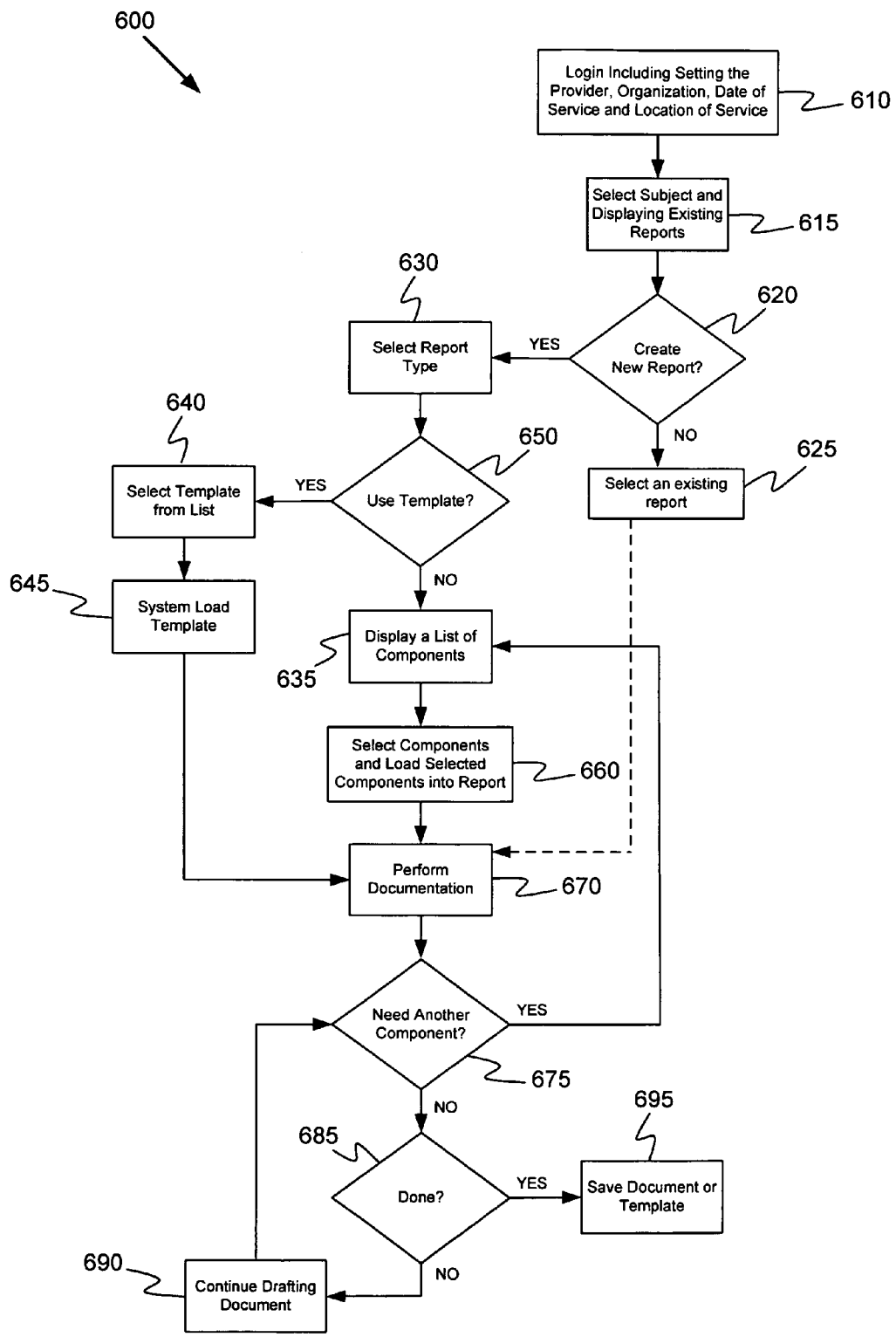
FIG. 6 is a flowchart illustrating a computer-based method of generating a report according to an exemplary embodiment of the present invention.

FIG. 6 is a flowchart illustrating a computer-based method of generating a report according to an exemplary embodiment of the present invention.

Referring to FIG. 6, in a step 610, a user logs onto a computer system and sets up report parameters that may include provider information, organization information, date of service, location of service, etc. In a step 615, the user selects what is to be the subject of the report and a list of pre-defined existing reports for that subject are presented. In a step 620, the user decides whether to create a new report for the entered subject. In a step 625, instead of creating a new report, the user can select an existing report. Once an existing report has been selected, it will be loaded and the report is ready for editing in a step 670.

When the user chooses to create a new report, they are presented with a list of report types for selection in a step 630. Once a report type is selected, the user has the option of using a template in a step 650. A report template is composed of pre-defined report components. If the user decides to use a template, a list of pre-defined templates is provided for selection in a step 640, the system loads the selected template into the report in a step 650, and the report is ready for editing in the step 670. However, if the user decides not to use a template, they are presented with a list of report components in a step 635. The user then selects a component for insertion into the report in a step 660 and the report is ready for editing in the step 670.

Once the report is ready for editing in the step 670, the user may begin entering data into previously inserted report components. The user may also continue to add more components in a step 675, thereby enabling the user to add report components to a report while editing the contents of report components currently in the report. Once the user is satisfied with the report they can either save the report or save the report as a template in a step 695. When a report is saved as a template, the report components as they are currently ordered in the report are stored within the template, any data entered in report components is stripped out, and the template may be inserted into the list of pre-defined templates. When a report is saved it may be inserted into the list of pre-defined existing reports.

Figure 7:
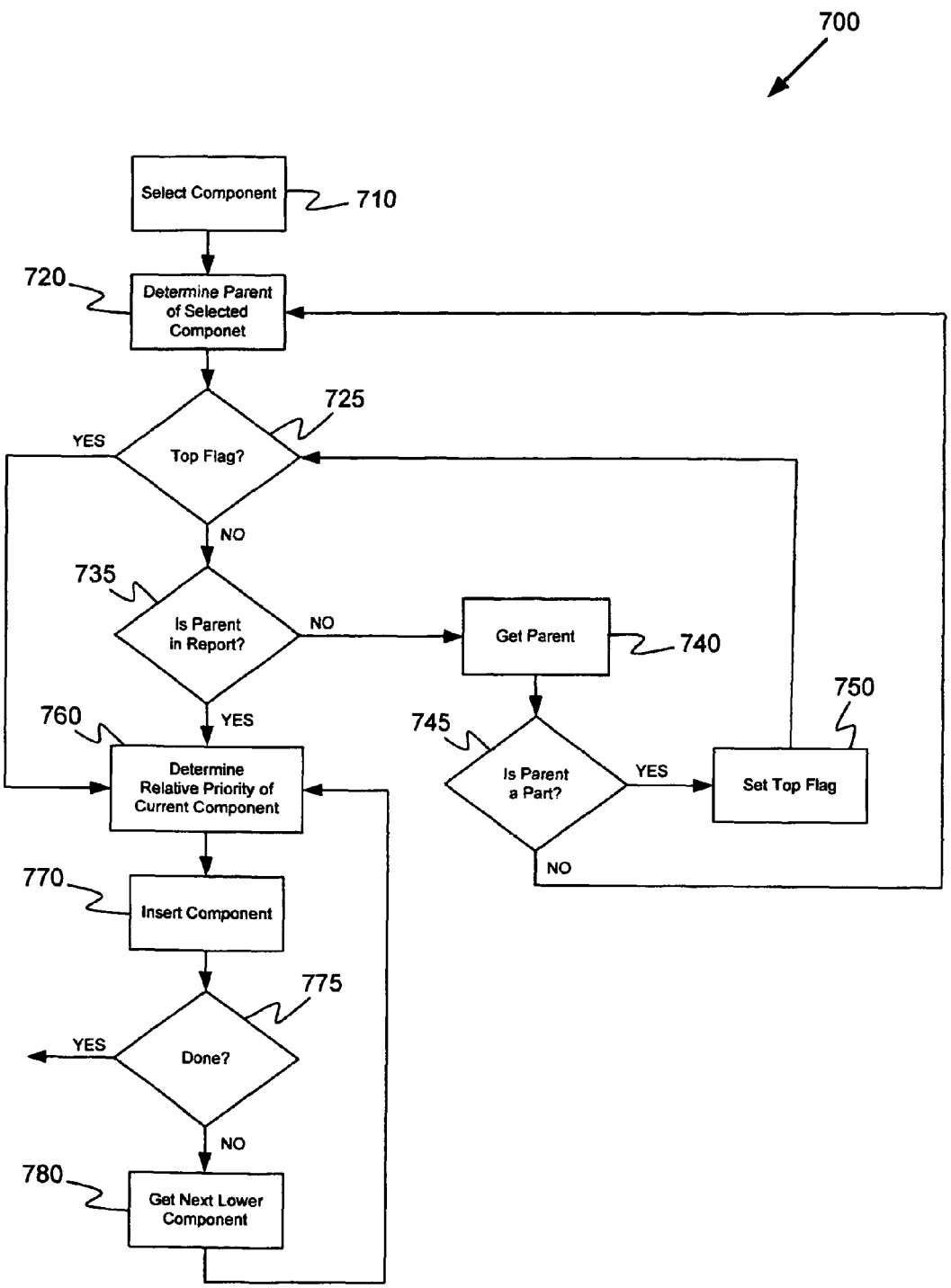
FIG. 7 is a flowchart illustrating the step of selecting and inserting a component into a report shown in FIG. 6, according to an exemplary embodiment of the present invention.

FIG. 7 is a flowchart illustrating the step of selecting and inserting a report component into a report shown in FIG. 6, according to an exemplary embodiment of the present invention.

Referring to FIG. 7, a user selects a report component for insertion into a report in a step 710. A parent of the selected component is determined in a step 720. Whether the parent is in the report is then determined in a step 735. If the parent is not in the report, it is retrieved as the current component in a step 740. Whether the current component is a report part is then determined in a step 745. Assuming the current component is a part, a top flag is set in a step 750. The relative priority of the current component is determined in a step 760 and inserted into the report in a step 770. The selected component is retrieved in a step 780 and inserted based on the relative priority of the selected component.

Figure 8:
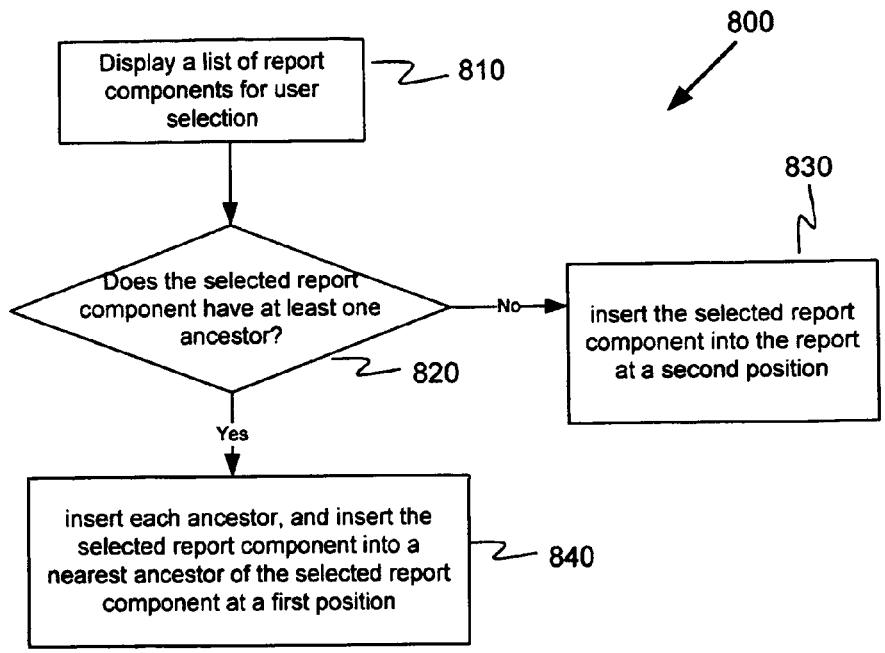
FIG. 8 is a flowchart illustrating a method of generating a report according to an exemplary embodiment of the present invention.

FIG. 8 is a flowchart illustrating a method of generating a report according to an exemplary embodiment of the present invention.

Referring to FIG. 8, in a step 810, a list of report components is displayed for user selection. In a step 820, whether the selected report component has at least one ancestor is determined. A report component without any ancestors is already at the highest level of a report. In an exemplary embodiment of the invention, a report component without ancestors is a report part. In a step 830, the report component is inserted into the report. In a step 840 the ancestors of the report component are inserted into the report and the report component is inserted into a nearest ancestor of the report.

Ancestors of a report component may be inserted into a report in a highest to lowest hierarchical level order. In an exemplary embodiment of the invention, the ancestors of a report subsection are a report subpart and a report part. Inserting the ancestors in highest to lowest generational order means that the report part is entered before the report subpart because report subpart is a child of the report part.

Ancestors of a report component and a report component may be inserted into a report when not already present in the report to prevent duplicate report component entries.

Figure 9:
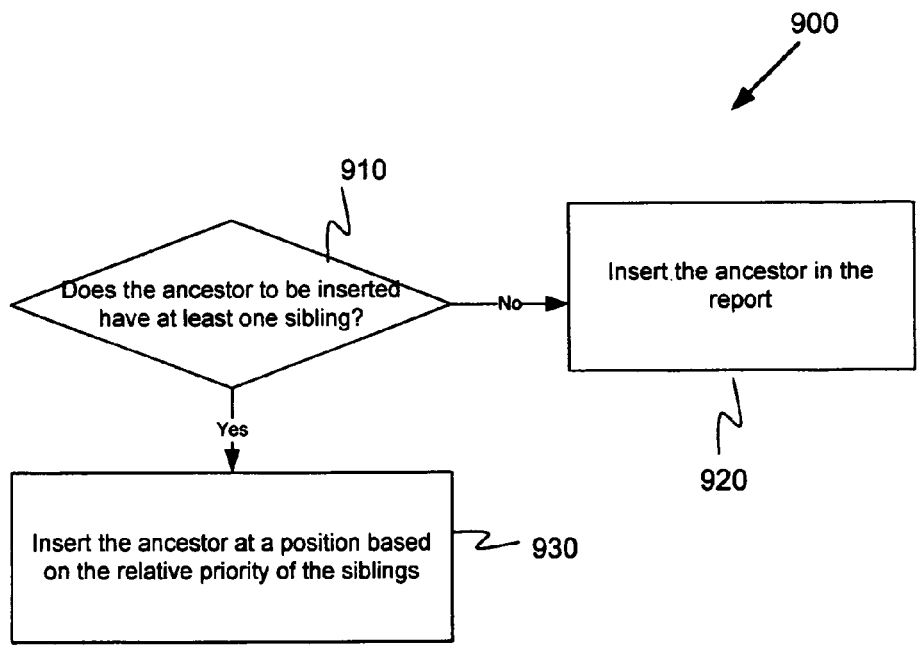
FIG. 9 is a flowchart illustrating the step of inserting an ancestor of the report component of FIG. 8, according to an embodiment of the present invention.

FIG. 9 is a flowchart illustrating the step of inserting an ancestor of a report component of FIG. 8 according to an embodiment of the present invention.

Referring to FIG. 9, in a step 910, whether an ancestor of a report component has a sibling report component is determined. In a step 920, the ancestor is inserted into the report. In a step 930, the ancestor is inserted into the report at a pre-determined second position based on the relative priorities of the siblings of the ancestor.

An ancestor of a report component with a priority equal to a sibling of the ancestor may be inserted into the report relative to the sibling of the ancestor based on alphabetic order of the ancestor and the sibling of the ancestor.

An ancestor of a report component may be entered into a parent of the ancestor when the ancestor is not at a highest generational level in the report.

Figure 10:
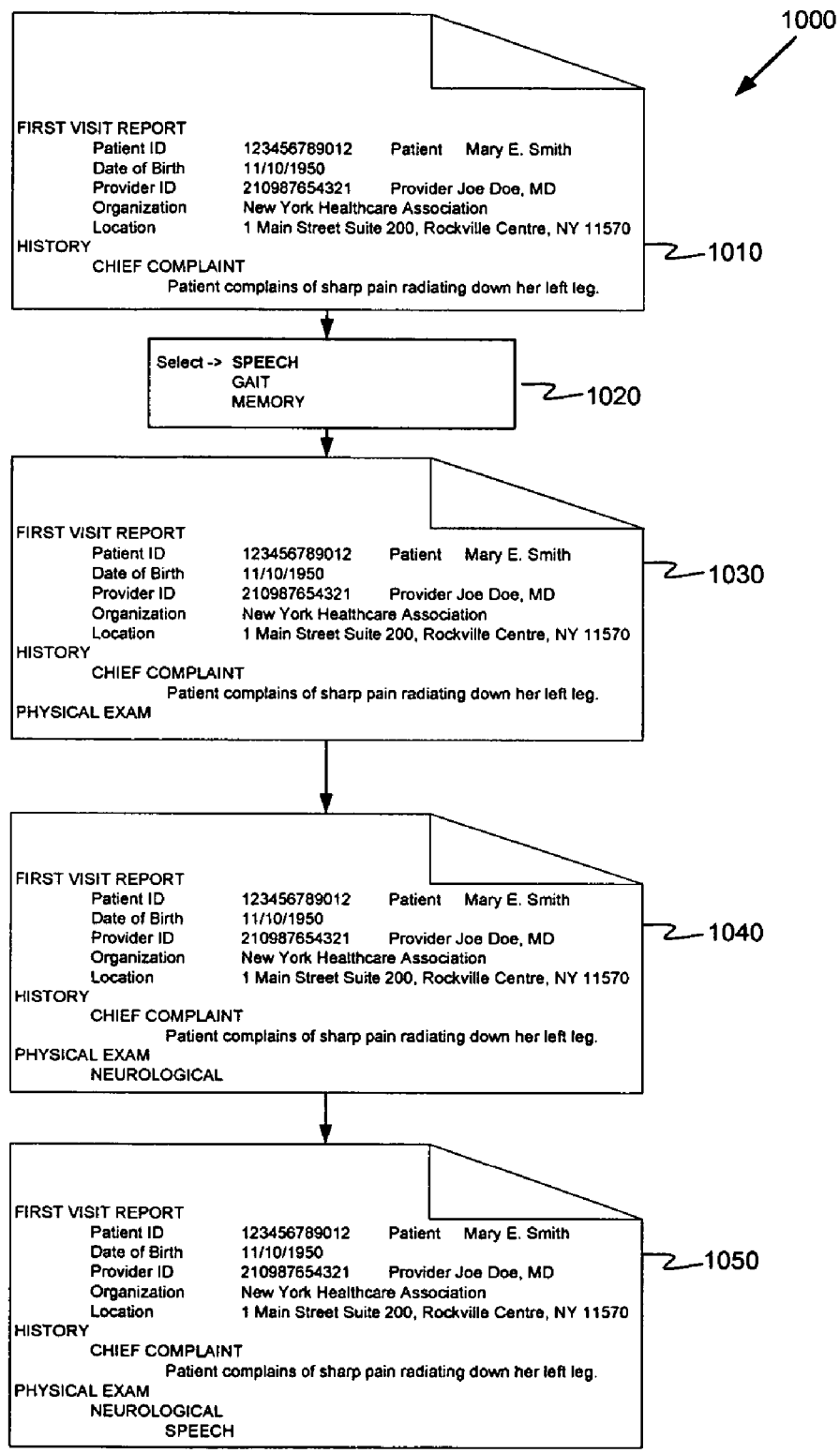
FIG. 10 is a diagram illustrating an example of how a report component is inserted into a medical report according to an exemplary embodiment of the invention.

FIG. 10 is a diagram illustrating an example of how a report component is inserted into a medical report according to an exemplary embodiment of the invention.

Referring to FIG. 10, in a step 1010, the medical report comprises a report header FIRST VISIT REPORT, a report part HISTORY, and a report section CHIEF COMPLAINT. The report header comprises a patient id, patient name, date of birth, provider id, provider name, organizational information, and location of service. The report header may contain various fields, as the report header of FIG. 10 is merely an exemplary embodiment.

In a step 1020, the user selects a medical report subsection SPEECH as the selected report component for insertion. Since the highest-level ancestor of SPEECH is a medical report part PHYSICAL EXAM, it is inserted next into the medical report in a step 1030. The medical report part PHYSICAL EXAM is inserted after the medical report part HISTORY because the priority of the PHYSICAL EXAM is lower then the medical report part HISTORY. Next a medical report subpart NEUROLOGICAL is inserted into the medical report in a step 1040. The medical report subpart NEUROLOGICAL is inserted below the medical report part PHYSICAL EXAM because it is a child of the medical report part PHYSICAL EXAM and the parent of the medical subsection SPEECH. Finally the medical report subsection SPEECH is inserted into the medical report subpart NEUROLOGICAL in a step 1050. The medical report subsection SPEECH is inserted below NEUROLOGICAL because it is a child of NEUROLOGICAL. If the medical report subpart NEUROLOGICAL had sibling subsections, the medical report subsection SPEECH would have been inserted relative to the priorities of the sibling subsections. The hierarchical relationships and component priorities embodied in FIG. 10 are merely examples for reference. The relationships and priorities of any medical report parts, subparts, sections, or subsections embodied in FIG. 10, may be varied.

According to an exemplary embodiment of the present invention, there is provided a computer-based method for building a template for use in generating a report. The report may include, but is not limited to including a medical report, a client report, a tax report, an accounting report, an accident report, an inventory report, an insurance report, a financial report, etc. The computer-based method includes inserting a selected report component into the template at a first position which is relative to a priority of the report component and priorities of all siblings of the report component, determining a template name based on user provided input, and storing the template using the template name.

The report component is selected by a user from a list of report components. The list of report components may be filtered so only a select set of report components are listed. This filtering may be based on various factors including report type, field of the report, subject of the report, profession of the user, etc.

The report component is inserted into the template at a position relative to other sibling report components that were previously inserted into the template. A sibling report component is a report component on the same hierarchical level as the inserted report component. As an example, a report part may contain two report sections. The two report sections would each be considered siblings of one another. The position of insertion is computed based on ordering priorities of the report component to be inserted and each of the sibling report components.

When a report component is selected for insertion into a template, ancestors of the report component not already present in the template, may be automatically inserted into the template. As an example, if a report subsection were selected for insertion into the template, a report subpart which is the parent of the report subsection, and a report part which is the parent of the report subpart would automatically be inserted into the template if they were not already present. An ancestor may be inserted into the template at a second position which is relative to the priority of the ancestor and priorities of sibling ancestors in the template.

Report components are divided into two main categories, structural components and EProbe components. The structural components are used to create the structure of a report and include report parts, report subparts, report sections, and report subsections.

Figure 11:
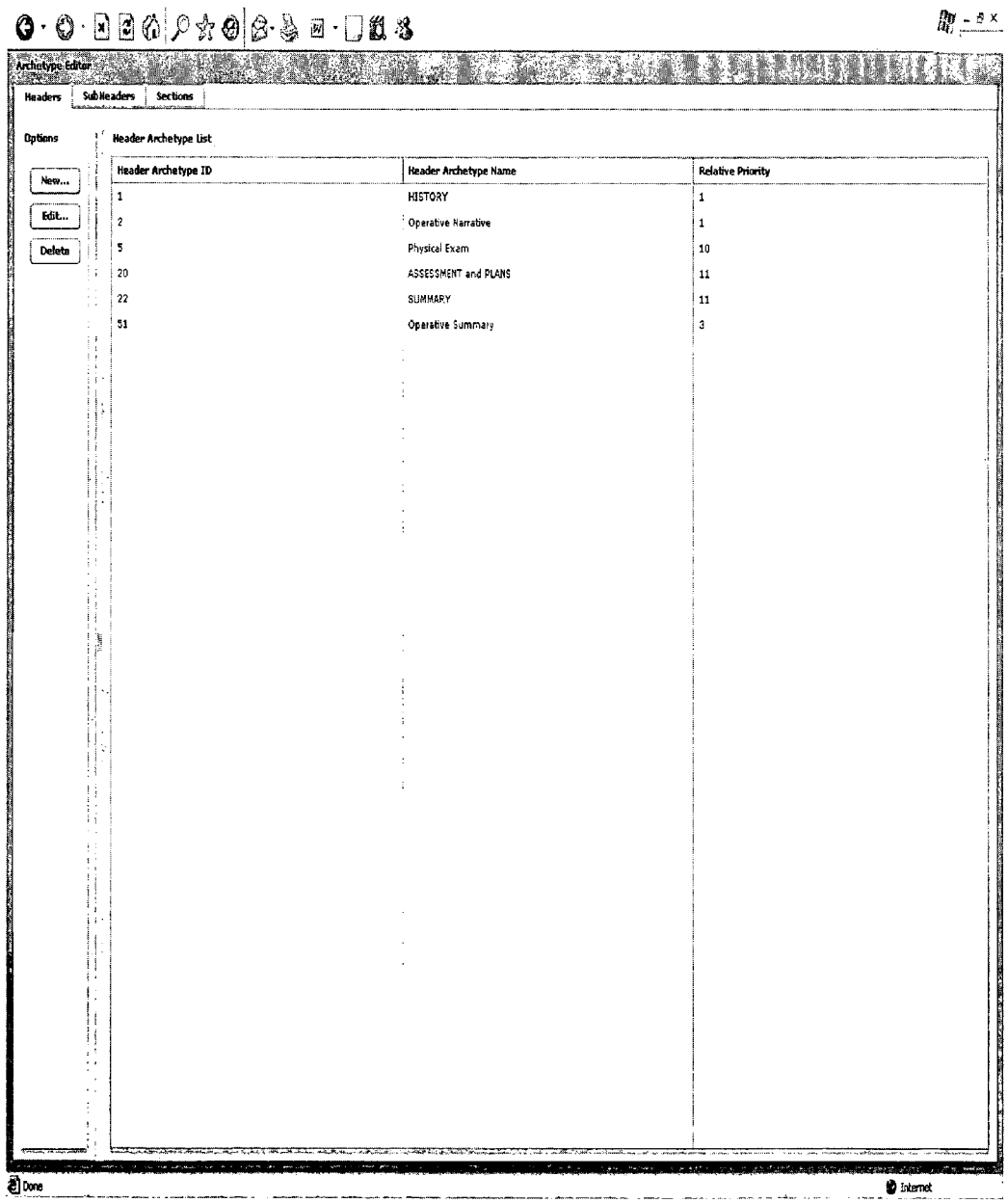
FIG. 11 illustrates report parts (illustrated as headers) in the Archetype Editor, according to an exemplary embodiment of the present invention.
Figure 12:
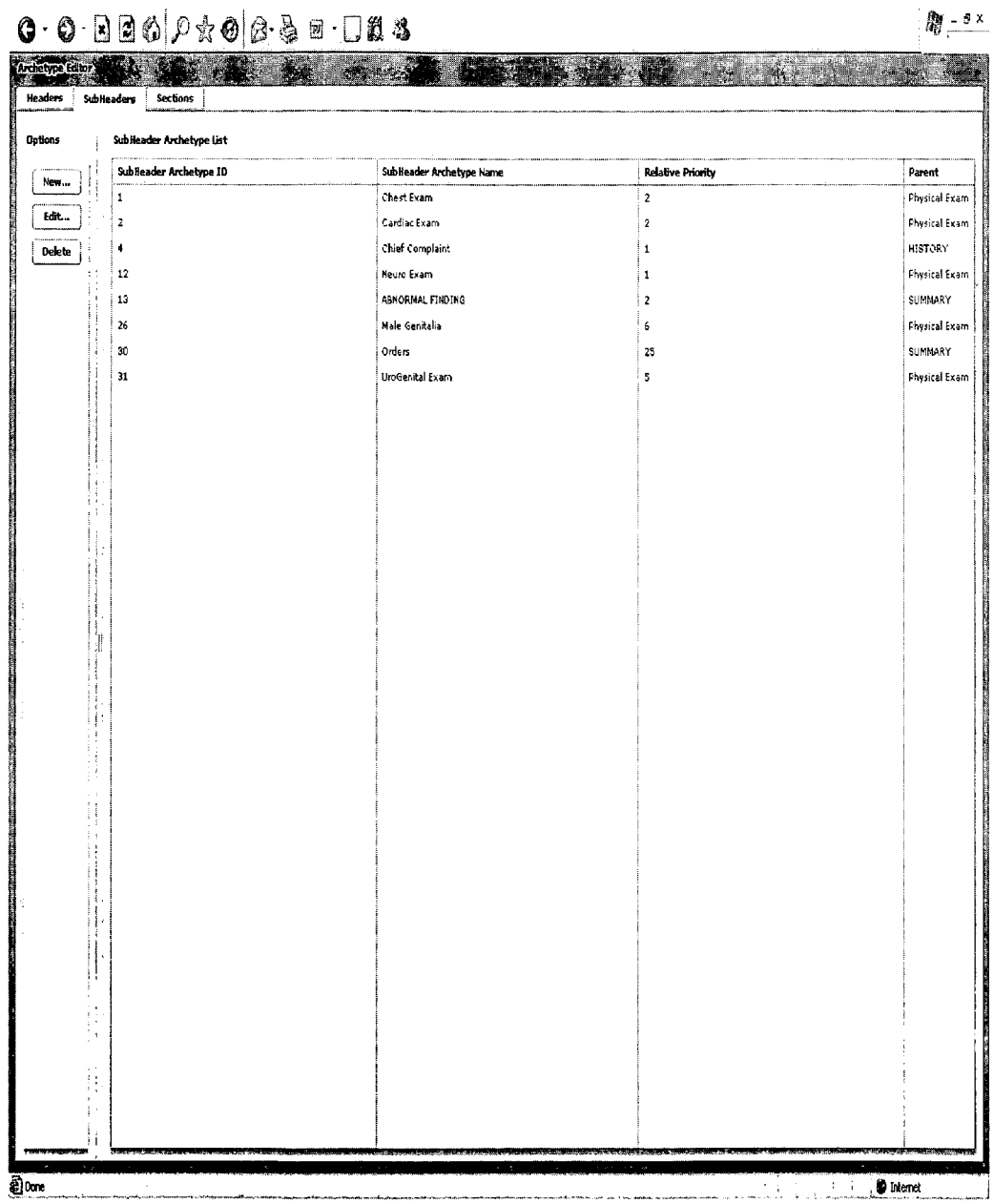
FIG. 12 illustrates report subparts (illustrated as subheaders) in the Archetype Editor, according to an exemplary embodiment of the present invention.
Figure 13:
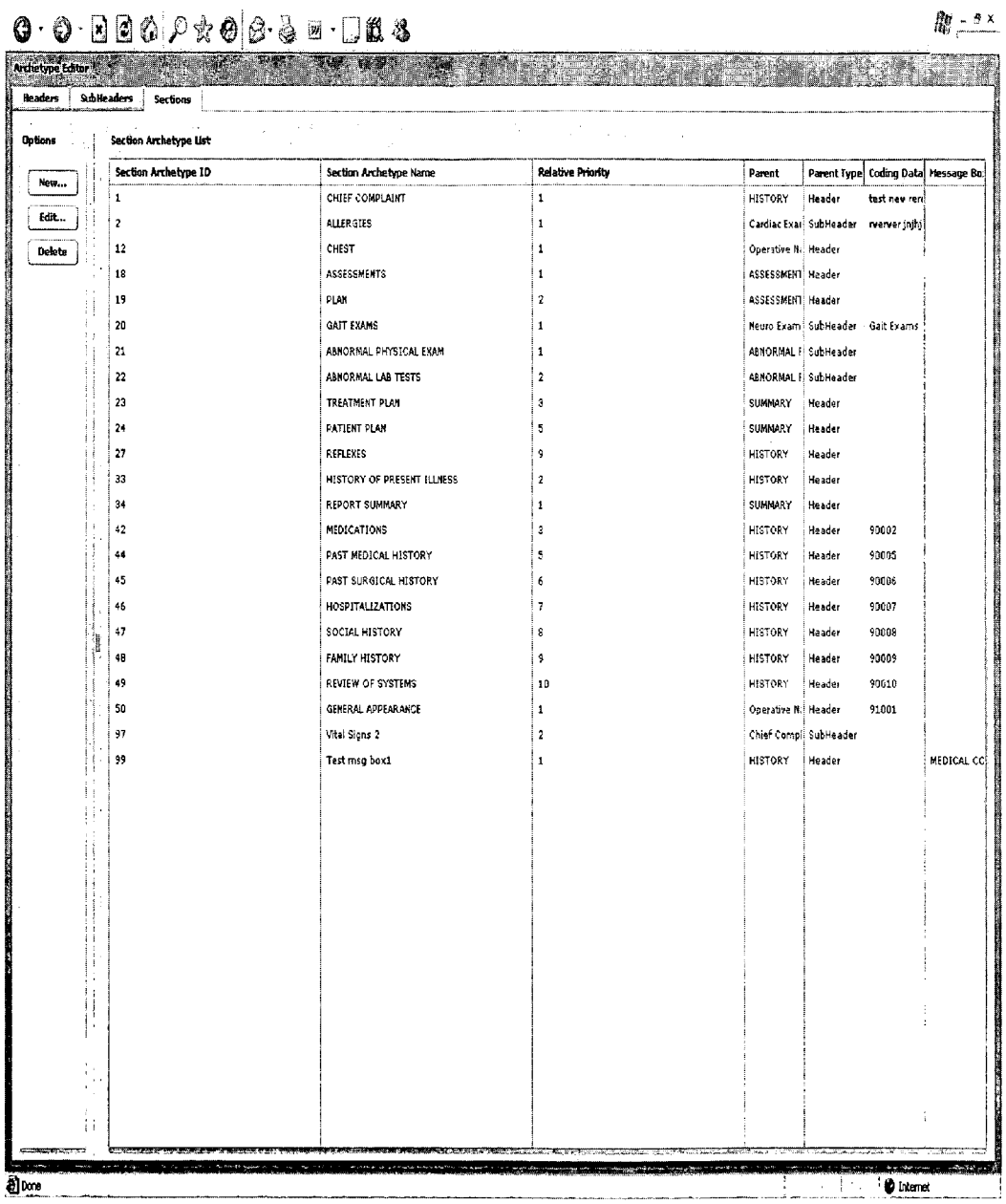
FIG. 13 illustrates report sections and subsections (both illustrated as section) in the Archetype Editor, according to an exemplary embodiment of the present invention.

FIGS. 11-13 illustrates exemplary aspects of an Archetype Editor which may be used to construct structural components such as report parts, subparts, sections and subsections according to an exemplary embodiment of the present invention. Referring to FIGS. 11-13, the tab labeled 'Headers' corresponds to report parts, the tab labeled 'SubHeaders' corresponds to report subparts, and the tab labeled 'Sections' corresponds to report sections and subsections. A subsection may be considered a section having a report subpart as a parent. The Archetype Editor is used to create and define properties of the structural components.

FIG. 11 illustrates report parts (illustrated as headers) in the Archetype Editor, according to an exemplary embodiment of the present invention. Each report part entry has a predefined unique id, a name, and a relative priority. A new report part can be generated by selecting the option labeled 'New'. An existing report part can be generated by selecting a report part entry and selecting the option labeled 'Edit'. An existing report part can be deleted by selecting a report part entry and selecting the option labeled 'Delete'. Once the 'Edit' or 'New' option has been selected, a popup window appears allowing the user to enter the name, the relative priority, etc. of the report part.

FIG. 12 illustrates report subparts (illustrated as subheaders) in the Archetype Editor, according to an exemplary embodiment of the present invention. Each report subpart entry has a predefined unique id, a name, a relative priority, and a parent. A new report subpart can be generated by selecting the option labeled 'New'. An existing report subpart can be edited by selecting a report subpart entry and selecting the option labeled 'Edit'. An existing report part can be deleted by selecting a report subpart entry and selecting the option labeled 'Delete'. Once the 'Edit' or 'New' option has been selected, a popup window appears allowing the user to enter the name, the relative priority, the parent, etc. of the report subpart.

FIG. 13 illustrates report sections and subsections (both illustrated as section) in the Archetype Editor, according to an exemplary embodiment of the present invention. Each entry has a predefined id, a name, a relative priority, a parent, a parent type, and additional related data. An entry with a parent type of 'Header' (also known as a report part) is a section and an entry with a parent type of 'SubHeader' (also known as a report subpart) is a subsection. A new report section or subsection can be generated by selecting the option labeled 'New'. An existing report section or subsection can be modified by selecting an entry and selecting the option labeled 'Edit'. An existing report section or subsection can be deleted by selecting an entry and selecting the option labeled 'Delete'. Once the 'Edit' or 'New' option has been selected, a popup window appears allowing the user to enter the name, the relative priority, the parent, the parent type, etc of the report section.

The Archetype Editor may be used to create structural components that are unique for a particular institution. As an example, even though all reports contain a report section called 'chief complaint', Hospital A may want to constrain the 'chief complaint' report section to prevent dictation.

The EProbe components provide a means of defining structured data sets for a section or a subsection of a report. The word probe is used to refer to a set of query/response pairs that can be used to collect information in an ordered, structured manner for inclusion in a report. The 'E' before EProbe refers to the word "embedded" because EProbe components are usually embedded within report sections or report subsections of a report.

Figure 14:
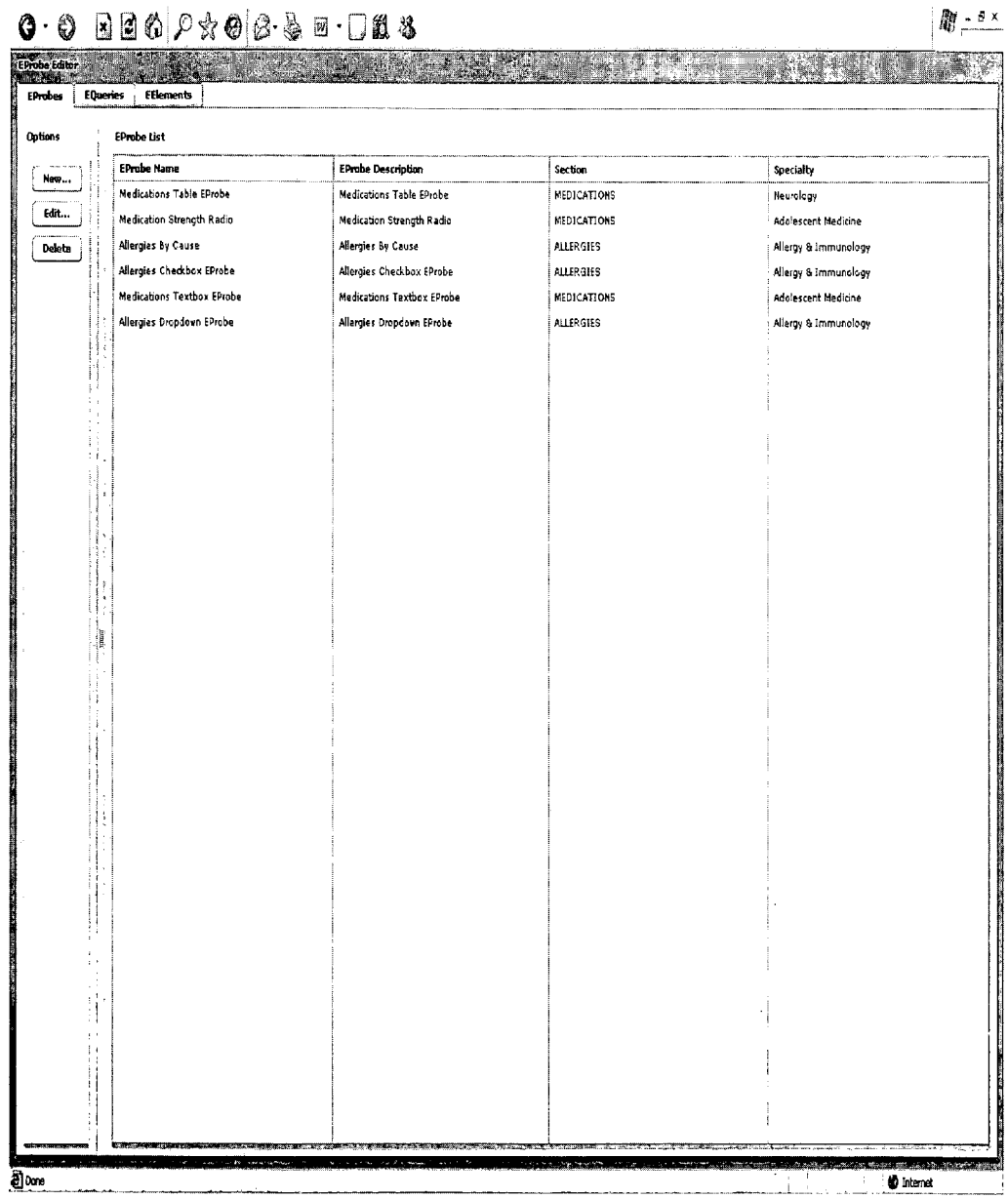
FIG. 14, FIG. 15, and FIG. 16 illustrate exemplary aspects of an EProbe Editor used to construct EProbe components for use with report sections and subsections according to an exemplary embodiment of the present invention.
Figure 15:
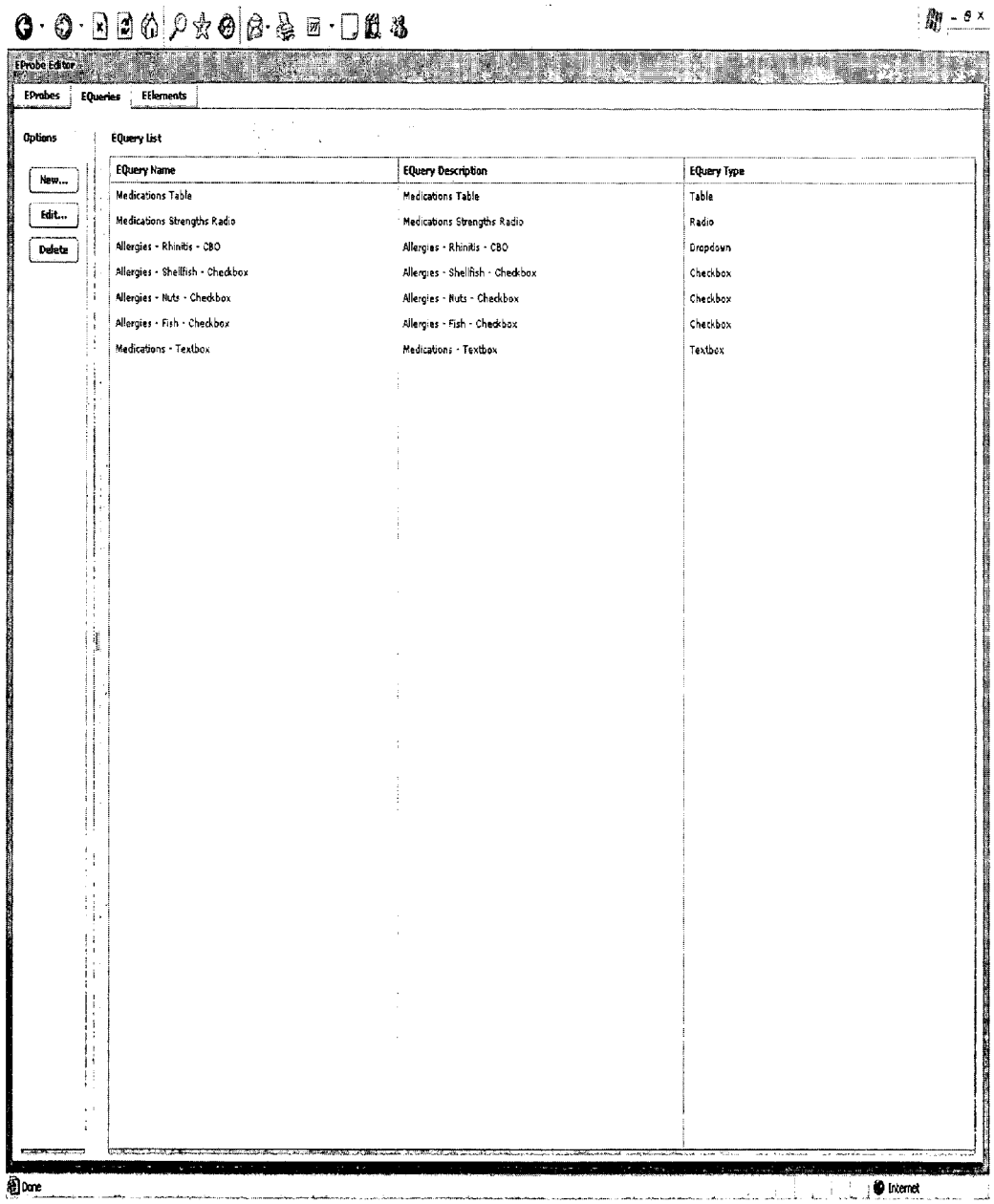
Figure 16:
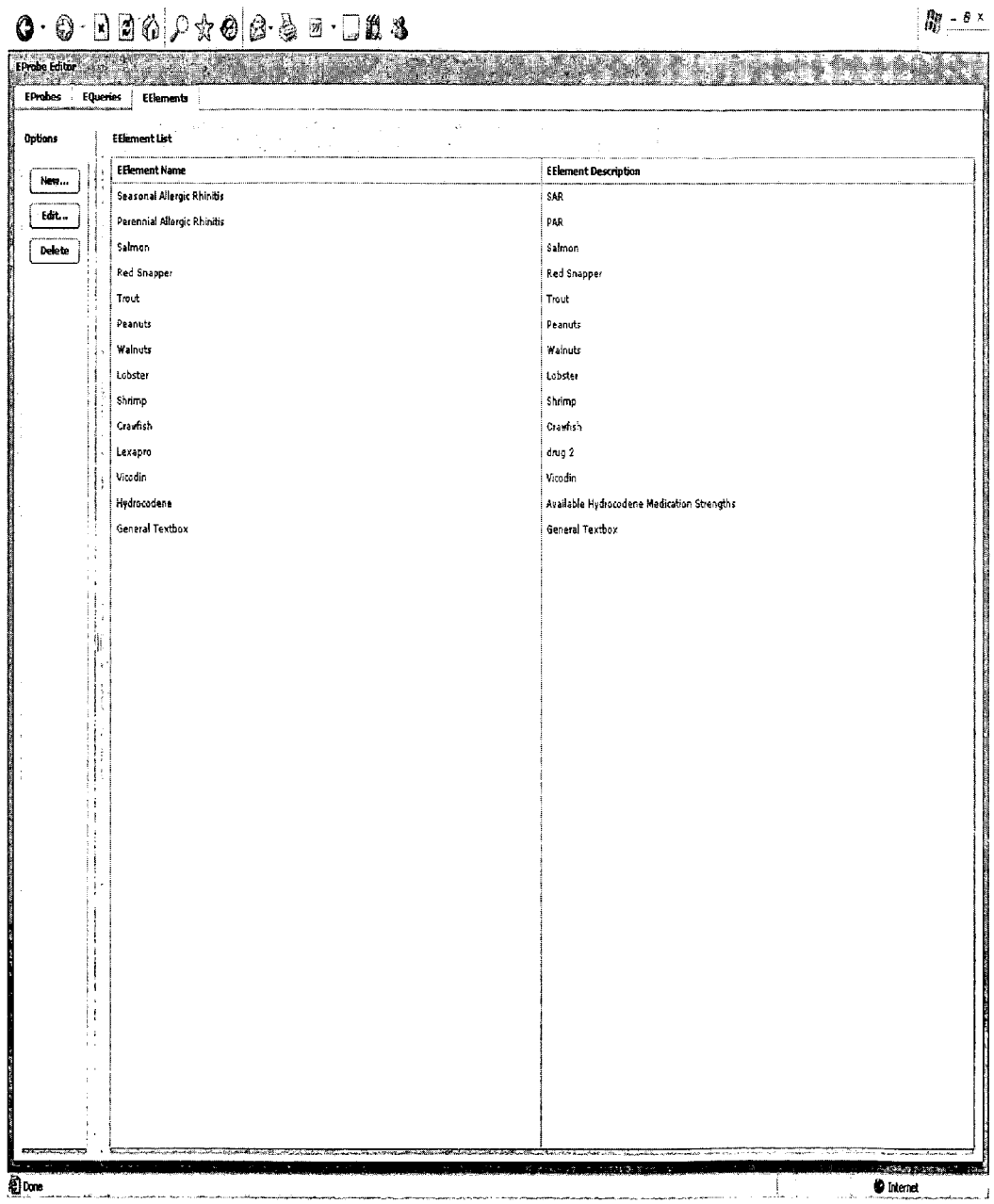

FIGS. 14-16 illustrates exemplary aspects of an EProbe Editor used to construct EProbe components for use with report sections and subsections according to an exemplary embodiment of the present invention.

Referring to FIGS. 14-16, the EProbe editor includes tabs labeled 'EProbes', 'EQueries', and 'EElements'. An EProbe component is a container for EQuery components and each EQuery component includes EElement components. EProbe components are reusable and may be found in multiple reports. EProbe properties determine how the EQuery components will be displayed.

Referring to FIG. 14, each EProbe component entry includes a name, a description, a section, a specialty, etc. As discussed above with respect to FIGS. 11-13, a section may represent a report subsection when its parent is a report subpart. An existing EProbe component can be deleted by selecting an EProbe component entry and selecting an option labeled 'Delete'. A new EProbe component can be generated by selecting an option labeled 'New'. An existing EProbe component can be edited by selecting an EProbe component entry and selecting an option labeled 'Edit'. Once the 'Edit' or 'New' option has been selected, a popup window appears allowing the user to enter the name, the description, the section, the specialty, any available EQuery components, etc.

Referring to FIG. 15, each EQuery component entry includes a name, a description, and a type. The type may include table, radio button, dropdown list, check box, text box, etc. An existing EQuery component can be deleted by selecting an EQuery component entry and selecting an option labeled 'Delete'. A new EQuery component can be generated by selecting an option labeled 'New'. An existing EQuery component can be edited by selecting an EQuery component entry and selecting an option labeled 'Edit'. Once the 'Edit' or 'New' option has been selected, a popup window appears allowing the user to enter the name, the description, the type, any available EElements, etc.

Referring to FIG. 16, each EElement component entry includes a name and a description. An existing EElement component can be deleted by selecting an EElement component entry and selecting an option labeled 'Delete'. A new EElement component can be generated by selecting an option labeled 'New'. An existing EElement component can be edited by selecting an EElement component entry and selecting an option labeled 'Edit'. Once the 'Edit' or 'New' option has been selected, a popup window appears allowing the user to enter the name, the description, and any appropriate data.

For example, an EProbe component for a structured data set for a section entitled "vital signs" might contain four EQueries: (1) blood pressure, (2) heart rate and rhythm, (3) respiratory Rate, and (4) body temperature and site measured. An EQuery component may include more than one datum. For example, the EQuery component for blood pressure could contain three datum: (1) systolic blood pressure, (2) diastolic blood pressure, and (3) patient position when blood pressure measured.

An EProbe component may include a variety of different formats including: list, table, icon/pictured based, etc. For example, a list of allergies could use a table based EProbe component and the columns of the table could include: (1) agent, (2) reaction, (3) date of first reaction, and (4) ever hospitalized for this allergy (Y/N). Each item in each row could represent a separate EQuery component or elements of the same EQuery component. The pictured based EProbe component could use a background picture or icon and be organized on a 2-D plane to demonstrate the data.

A single EQuery component may include multiple data elements, called EElements. For example, an EQuery component called blood pressure contains three EElements: SBP, DBP, and patient position. The latter is selected via a drop down list. The first two are selected via numerical scales.

The EProbe Editor allows the user to define the appearance of EQuery components and their corresponding EElements within a section or a subsection. For example, the section "tendon reflexes" can contain EQuery components for (1) right and left biceps, (2) right and left triceps, (3) right and left patellar, and (4) right and left Achilles reflexes. These EQuery Components may be represented by a list, a table, or a picture. For example, a picture of a stick figure can be added and the value of entry fields of the EQuery components discussed above can be given x,y coordinates relative to the picture for data entry. As an example, a right triceps reflex data entry field could be placed next to a right triceps in the stick figure picture.

The EProbe/EQuery/EElement data structures allow for (1) structured, predefined data sets for any section or subsection of a report and (2) allow the data to be stored not only in a textual report but in a standard database in a meaningful way. For example, a blood pressure EQuery component could be used in all reports by all doctors entering data into the "Vital Sign" section of a report. This would allow one to plot blood pressures recorded by all doctors using the system over many years to assess trends towards hypertension. It is to be further understood that, because some of the constituent system components and method steps depicted in the accompanying figures may be implemented in software, the actual connections between the system components (or the process steps) may differ depending upon the manner in which the present invention is programmed. Given the teachings of the present invention provided herein, one of ordinary skill in the related art will be able to contemplate these and similar implementations or configurations of the present invention.

Hereinafter, a computer readable medium including computer code for building a template for use in generating a report, in accordance with an exemplary embodiment of the present invention will be described. The computer readable medium comprises: computer code for determining a report component based on user input for insertion into the template, wherein the report component is inserted into the template at a position relative to a priority of the report component and priorities of all siblings of the report component; computer code for determining a template name based on user provided input; and computer code for storing the template using the template name.

According to an exemplary embodiment of the present invention, there is provided a computer readable medium including computer code for generating a report. The computer readable medium has computer code for initializing a plurality of report parameters, computer code for determining a report editing mode based on a selected report editing mode, computer code for generating a filtered list of report components based on the plurality of report parameters and the report editing mode, computer code for determining a report component based on selection from the filtered list of report components, and computer code for inserting the report component into the report at a pre-determined first position derived from a first priority of the report component. The plurality of report parameters may comprise a user identifier parameter, a date of service parameter, a provider organization identifier parameter, a client identifier parameter, a report subject matter parameter, and an account identifier parameter, etc. The first priority may be relative to a second priority of a second report component in the report. The computer code for inserting the report component may automatically insert a third report component into the report that is associated with the report component.

Although the exemplary embodiments of the present invention have been described in detail with reference to the accompanying drawings for the purpose of illustration, it is to be understood that the that the inventive processes and systems are not to be construed as limited thereby. It will be readily apparent to those of ordinary skill in the art that various modifications to the foregoing exemplary embodiments can be made therein without departing from the scope of the invention as defined by the appended claims, with equivalents of the claims to be included therein.

What is claimed is:

1. A computer-based method for generating a report, comprising:
 initializing report parameters;
 selecting a report editing mode;
 generating a filtered list of report components based on the initialized report parameters and the selected report editing mode;
 displaying the filtered list of report components for user selection;
 selecting one of the report components from the displayed list;
 if the selected report component has one or more ancestor report components, inserting each of the one or more ancestor report components into the report and inserting the selected report component into a nearest ancestor report component of the selected report component; and
 if the selected report component does not have an ancestor report component, then:

determining whether the selected report component has at least one sibling report component, and if the selected report component does have at least one sibling report component, inserting the selected report component and the associated at least one sibling report component into the report based on priorities for the selected report component and the associated at least one sibling report component, or if the selected report component does not have at least one sibling report component, inserting the selected report component into the report at a first predetermined position.

2. The computer-based method of claim 1, wherein, when the selected report component has at least one sibling report component and the priorities of the selected report component and the associated at least one sibling report component are equal, the selected report component and the associated at least one sibling report component are ordered alphabetically relative to one another.

3. The computer-based method of claim 1, wherein each ancestor report component that is to be inserted into the report is inserted only when it is not already in the report, and wherein the selected report component that is to be inserted into the report is inserted only when it is not already in the report.

4. The computer-based method of claim 1, wherein the report comprises a report header containing information about the report derived from the step of initializing report parameters.

5. The computer-based method of claim 1, wherein determining a report editing mode comprises:

determining whether a new report choice or an existing report choice has been selected from user input;

if the new report choice has been selected, displaying a list of pre-defined report types, and determining the report type based on a user selection of the list of pre-defined report types; and if the existing report choice has been selected, displaying a list of pre-defined existing reports, and determining the report type based on user selection of the list of pre-defined existing reports.

6. The computer-based method of claim 5, wherein if the new report choice has been selected further comprises:

displaying a list of pre-defined templates; and inserting a selected template into the report.

7. The computer-based method of claim 5 further comprising:

generating a new template from the report;

storing the new template; and inserting the new template into a list of pre-defined templates.

8. The computer-based method of claim 5, further comprising:

storing the report; and inserting the report into the list of pre-defined existing reports.

9. A computer-based method for generating a report, comprising:

initializing report parameters:

selecting a report editing mode;

generating a filtered list of report components based on the initialized report parameters and the selected report editing mode;

displaying the filtered list of report components for user selection;

selecting one of the report components from the displayed list;

if the selected report component has one or more ancestor report components, inserting each of the one or more ancestor report components into the report and inserting the selected report component into a nearest ancestor report component of the selected report component, wherein inserting each of the one or more ancestor report components into the report comprises:

ordering the one or more ancestor report components;

inserting the one or more ancestor report components into the report based on the ordering; and if any of the ordered one or more ancestor report components have at least one sibling report component, inserting the associated at least one sibling report component into the report based on priorities for the ancestor report component and the associated at least one sibling report component, and if the selected report component does not have an ancestor report component, inserting the selected report component into the report at a first pre-determined position.

10. The computer-based method of claim 9, wherein inserting the selected report component into the report automatically inserts a second report component into the report, wherein the second report component is derived from a pre-defined rule for the selected report component.

11. The computer-based method of claim 9, wherein the ordering of the one or more ancestor report components is from highest level to lowest level.

12. The computer-based method of claim 9, wherein, when the ordered one or more ancestor report components have at least one sibling report component and the priorities of the ancestor report component and the associated at least one sibling report component are equal, the ancestor report component and the associated at least one sibling report component are ordered alphabetically relative to one another.

13. The computer-based method of claim 9, wherein inserting the ancestor into the report comprises:

determining if an ancestor report component that is to be inserted has a parent in the report; and if the ancestor report component that is to be inserted has a parent in the report, inserting the ancestor report component into the parent.

* * * * *